(12) United States Patent
Wiede, Jr. et al.

(10) Patent No.: US 6,764,660 B1
(45) Date of Patent: Jul. 20, 2004

(54) PROCESS AND APPARATUS FOR CONTROLLING REACTION TEMPERATURES WITH HEATING ARRANGEMENT IN SERIES FLOW

(75) Inventors: William Wiede, Jr., Villa Park, IL (US); Kevin J. Brandner, Bartlett, IL (US); Bruce A. Briggs, Carol Stream, IL (US); Donald E. Felch, Arlington Heights, IL (US); Constante P. Tagamolila, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 536 days.

(21) Appl. No.: 09/593,789

(22) Filed: Jun. 14, 2000

Related U.S. Application Data

(62) Division of application No. 09/149,867, filed on Sep. 8, 1998, now Pat. No. 6,100,436.

(51) Int. Cl.[7] ............................. F28D 7/00; B01J 35/02
(52) U.S. Cl. ...................... 422/198; 422/176; 422/173; 422/177; 422/180; 422/200; 422/201; 422/211; 422/222; 165/104.19; 165/104.28; 165/104.34; 165/113
(58) Field of Search ................................ 422/176, 201, 422/173, 177, 180, 198, 211, 227, 200; 165/104.19, 104.28, 104.34, 113

(56) References Cited

U.S. PATENT DOCUMENTS

| | | | |
|---|---|---|---|
| 5,073,352 A | 12/1991 | Dang Vu et al. | 422/213 |
| 5,525,311 A | 6/1996 | Girod et al. | 422/200 |
| 5,554,347 A | * 9/1996 | Busson et al. | 422/204 |
| 5,600,052 A | 2/1997 | Girod et al. | 585/654 |
| 5,600,053 A | 2/1997 | Girod et al. | 585/654 |

* cited by examiner

Primary Examiner—Glenn Caldarola
Assistant Examiner—Alexis Wachtel
(74) Attorney, Agent, or Firm—John G. Tolomei; James C. Paschali

(57) ABSTRACT

A process and apparatus for contacting reactants with a particulate catalyst while indirectly heating the reactants with a heat exchange medium improves temperature control by using an intermediate heat exchange fluid and system to prevent overheating of reactants and maintain parallel heating characteristics through multiple reaction-heat exchange zones. The internal flow path minimizes the circulation of the reaction zone heat exchange fluid by incorporating interstage reheating of the reaction zone heat exchange fluid as it passes in series flow. A particularly useful application of the process and apparatus is in the dehydrogenation of ethylbenzene to produce styrene. The process and apparatus can also be used with simultaneous exchange of catalyst particles by an operation that restricts reactant flow while moving catalyst through reaction stacks in which the reactant flow has been restricted.

8 Claims, 9 Drawing Sheets

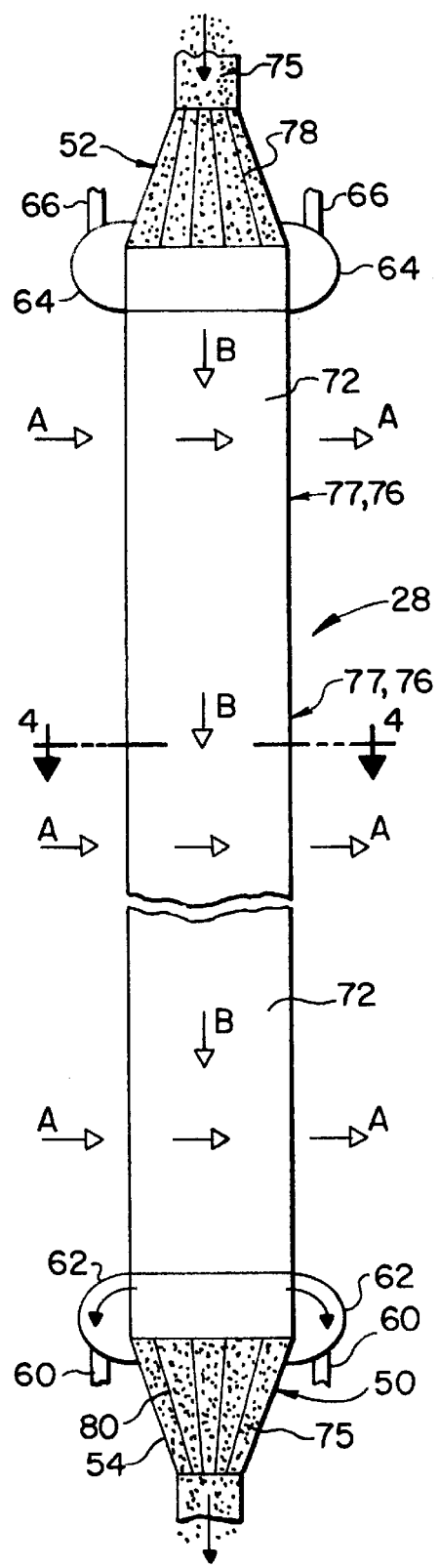
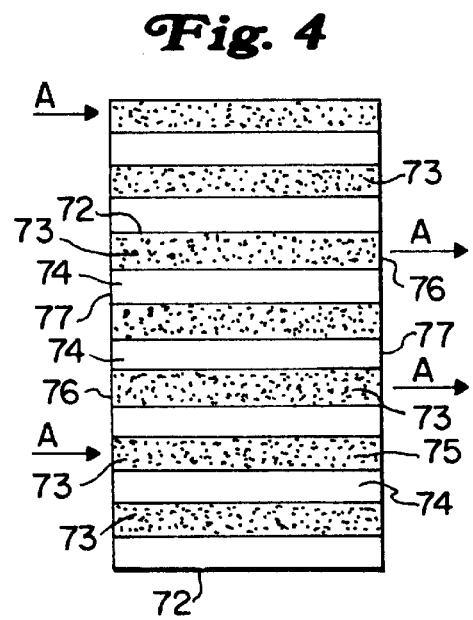
Fig. 4
Fig. 3

PROCESS AND APPARATUS FOR CONTROLLING REACTION TEMPERATURES WITH HEATING ARRANGEMENT IN SERIES FLOW

CROSS-REFERENCE TO RELATED APPLICATION

This application is a Division of application Ser. No. 09/149,867 filed Sep. 8, 1998, now U.S. Pat. No. 6,100,436, the contents of which are hereby incorporated by reference.

FIELD OF THE INVENTION

This invention relates to chemical reactors for the conversion of a reaction fluid while indirectly heating a reaction with a heat exchange fluid.

BACKGROUND OF THE INVENTION

In many industries, like the petrochemical and chemical industries for instance, the processes employ reactors in which chemical reactions are effected in the components of one or more reaction fluids by contact with a catalyst under given temperature and pressure conditions. Most of these reactions generate or absorb heat to various extents and are, therefore, exothermic or endothermic. The heating or chilling effects associated with exothermic or endothermic reactions can positively or negatively affect the operation of the reaction zone. The negative effects can include among other things poor product production, deactivation of the catalyst, production of unwanted by-products, and in extreme cases, damage to the reaction vessel and associated piping. More typically, the undesired effects associated with temperature changes will reduce the selectivity or yield of products from the reaction zone.

One solution to the problem has been the indirect heating of reactants and/or catalysts within a reaction zone with a heating or cooling medium. The most well known catalytic reactors of this type are tubular arrangements that have fixed or moving catalyst beds. The geometry of tubular reactors poses layout constraints that require large reactors or limit throughput.

Indirect heat exchange has also been accomplished using thin plates to define alternate channels that retain catalyst and reactants in one set of channels and a heat transfer fluid in alternate channels for indirectly heating or cooling the reactants and catalysts. Heat exchange plates in these indirect heat exchange reactors can be flat or curved and may have surface variations such as corrugations to increase heat transfer between the heat transfer fluids and the reactants and catalysts. Although the thin heat transfer plates can, to some extent, compensate for the changes in temperature induced by the heat of reaction, not all indirect heat transfer arrangements are able to offer the complete temperature control that would benefit many processes by maintaining a desired temperature profile through a reaction zone. Many hydrocarbon conversion processes will operate more advantageously by maintaining a temperature profile that differs from that created by the heat of reaction. In many reactions, the most beneficial temperature profile will be obtained by substantially isothermal conditions. In some cases, a temperature profile directionally opposite to the temperature changes associated with the heat of reaction will provide the most beneficial conditions. An example of such a case is in dehydrogenation reactions wherein the selectivity and conversion of the endothermic process is improved by having a rising temperature profile or reverse temperature gradient through the reaction zone. A specific arrangement for heat transfer and reactant channels that offers more complete control can be found in U.S. Pat. No. 5,525,311, the contents of which are hereby incorporated by reference.

Heating reactants within a reaction zone poses a number of limitations on the reactor arrangement and the operation of the process. A heat exchange reactor typically needs to operate with a large fluid mass flow rate of the heat transfer fluid in order to provide adequate mass flux of the heat transfer fluid over the heat transfer surfaces. Failure to maintain the adequate heat transfer fluid mass flux across the heat transfer surfaces will result in inadequate heating and a loss of benefit from providing the internal heating within the reaction zone. The heat exchange reaction section may be divided into multiple heat exchange reactor sections. Nevertheless each heat exchange reactor section still requires a high mass flux rate to provide adequate heating across all of the heat transfer surfaces.

Even with separate reaction zones or reaction stacks, as they are referred to herein, the maximum temperature for the heat transfer fluid also remains limited. Constraints on the temperature of the heat transfer fluid as providing heating to the reactants can typically apply to minimum or maximum values. Minimum allowable temperature must be high enough to induce a reaction rate that exceeds what would ordinarily be obtained from an adiabatic process. However, at the same time, the maximum temperature at which the heating fluid enters the heat transfer zone must not heat the reactants to a temperature that can cause a lack of selectivity in the products produced, or worse, a decomposition of the products already produced.

For example, in the dehydrogenation of ethylbenzene, the process requires that the endothermic heat of reaction be supplied internally or externally. In an adiabatic reactor operation, the sensible heat in the feed stream provides the endothermic heat of reaction. Mixing a large quantity of super heated steam to the ethylbenzene feed increases the available sensible heat. Limitations in the ability to provide heating by sensible heat restricts the maximum allowable temperature drop across the reactor. However, using excessive steam temperatures to maintain a minimum reaction temperature will exceed the maximum sensitivity temperature for the ethylbenzene and begin its decomposition. Furthermore, designing equipment for the more severe operating conditions significantly increases its cost. Again, the endothermic heat of reaction may also be supplied by indirect heat exchange from an appropriate heat transfer fluid. Nevertheless, providing sufficient mass flux to all of the heat transfer surfaces will require a high heat transfer fluid mass flow rate which would lead to larger equipment sizes and higher processing costs.

Accordingly, it is an object of this invention to reduce the heat transfer fluid mass flow rate required to provide the necessary heat transfer fluid mass flux to maintain a high reaction temperature without exceeding the sensitivity temperature of the reactants or the products produced by their reaction.

It is a further object of this invention to provide a reactor apparatus for the indirect heating of a reactant stream in a reaction zone while conserving heat and reducing the necessary mass flow rate to provide a given mass flux over the heat transfer surfaces.

BRIEF SUMMARY OF THE INVENTION

This invention uses a multiple-pass heat exchange configuration to heat reactants indirectly with a heat exchange fluid in groups of stacked plates that provide reaction zones having reaction channels and heat exchange channels. The multiple pass arrangement of this invention significantly improves heat transfer. In turn the multiple-pass heat exchanger effectively reduces the heat transfer fluid mass flow rate for endothermic reacting systems while maintaining the equivalent overall heat flux across the heat transfer surfaces that separate the reaction channels from the heating channels. This arrangement reduces the size of the heat transfer equipment. The invention may also be used to increase the heat flux while maintaining a constant heat transfer fluid mass flow rate. The invention uses a series flow of the heat transfer fluid through reactors that receive a parallel flow of reactants. This combination of flows permits the control of the process site temperature profiled in the reactant channels to a variety of desired shapes. The process also enhances the isothermal operation of a reaction zone by more uniformly distributing heat along the catalyst beds. The arrangement improves process and heat transfer flow distributions for co-current, counter-current, or cross-current operations. Serial flow maintains the heat transfer fluid mass flow rates across the heating channels for multiple reaction stacks and reduces capital and operating costs thereby lowering equipment sizes and utility requirements. The flexibility for controlling the temperature of the heat transfer fluid facilitates the use of a variety of heat transfer fluids such as steam, flue gas, liquid sodium, molten salt, and in-situ combustion to be used more efficiently.

This invention can be particularly useful with the use of high heat capacity heating fluids such as molten salts and liquid metals. In particular, liquid sodium has a heat capacity and thermal conductivity that are, on a volumetric basis, superior to most heat transfer mediums. Liquid sodium is known to work for use in dehydrogenation processes including paraffins and aromatics. Despite its excellent heat transfer properties even an excellent heating medium such as liquid sodium may require a mass ratio of heating fluid to process feed as high as 30 to obtain isothermal profiles. The heat transfer piping circulates liquid sodium or other heating fluid the multiple reaction stacks in series flow while the process piping passes the feed through the reaction stacks in parallel. In this manner, for each reaction stack or individual heat transfer reactor provided: in parallel, the mass flow rate of the process feed is reduced inversely to the total number of parallel reaction zones while the total of the heating fluid mass flux to heat transfer surfaces is maintained through the reheating of the heating fluid between the series of reactors. The heating fluid of this invention is not limited to liquid metal or molten salts and may include lower heat capacity fluids such as, hot oil, steam, or flue gas. The reheating of flue gas may be improved by the addition of small amounts of methane or other flue for direct combustion in the heat transfer medium.

The invention may be particularly useful for providing a heating fluid by catalytic combustion of a fuel stream. The rate of combustion of the fuel mixture could be controlled thereby distributing the heat release across more of the heat transfer surface to improve the process reaction profile in terms of selectivity and activity in the reaction channels.

This invention has been found to be particularly effective in the dehydrogenation of ethylbenzene to produce styrene. By improving the uniformity of the heat transfer rate across a heat transfer surface, this invention increases the selectivity for styrene production by up to 1.2% over traditional ethylbenzene dehydrogenation processes. Where steam was used as the heating fluid, the invention improved the usual production over that achieved by adiabatic reactors through the use of multiple-stage heating fluid flow through a plurality of parallel ethylbenzene dehydrogenation reactors. In particular, this invention improves the use of steam as a heating medium in the ethylbenzene dehydrogenation process. Processes for the production of styrene typically require a large amount of steam. This invention uses the steam first as the heating fluid and then injects the steam after heat transfer into the process feed to satisfy the required steam-to-oil ratio. Low steam-to-oil ratios are preferred to reduce utilities and operating costs. This invention facilitates the use of low steam mass flow rates while still providing the necessary heating into the reaction channels. Metallurgical limitations of the reactor will generally restrict steam temperatures to below 800° C. and, more practically, to below 650° C. This invention increases the heat flux for the steam by piping the steam in series to the heating channels of the reaction stacks and by reheating the steam up to 16 times.

Accordingly, in one embodiment, this invention is a process for contacting reactants with a particulate catalyst in a channel reactor while indirectly contacting the reactants with a heating fluid. The process retains catalyst particles in a plurality of reaction stacks. Each reaction stack contains a plurality of vertically and horizontally extended reaction channels in a plurality of vertically and horizontally extended heating channels for providing indirect heat exchange. A reactant stream passes to at least two of the reaction stacks in parallel flow and contacts the catalyst therein. A heating fluid passes through the heat exchange channels of at least two reaction stacks to create series flow of heating fluid through the reaction stacks. The heating fluid undergoes reheating as it passes from one reaction stack to another reaction stack. The heating fluid is recovered from the last reaction stack in the series of reaction stacks. At least a portion of the heating fluid returns to the first reaction stack in the series. The process recovers a reactant stream from the plurality of reaction stacks.

In another embodiment, this invention is a channel reactor apparatus for contacting reactants with a particulate catalyst, indirectly heating the reactants with a heating fluid and reheating the heating fluid with a heat source in a heater. The apparatus contains a plurality of reaction stacks with each reaction stack comprising a plurality of parallel plates extending vertically and horizontally. The reaction stacks define heating channels and reaction channels. A distribution system passes a reactant stream to the reaction channels of each reaction stack in parallel flow. A withdrawal system collects the parallel flows of reacted reactants from each reaction stack. The heating fluid delivery conduit delivers a heating fluid to the heating channels of one of the reaction stacks located in a lead position. A plurality of intermediate conduits pass the heating fluid in series flow from the reaction stack in the lead position through the heating channels of reaction stacks located in the intermediate position and finally to a reaction stack located in an end position. A heating fluid recovery conduit recovers the heating fluid from the reaction stack in the end position. A heater reheats the heating fluid that passes through each intermediate conduit.

Additional embodiments, arrangements, and details of this invention are disclosed in the following detailed description of the invention.

BRIEF DESCRIPTION OF THE DRAWINGS

FIG. 3 is a schematic representation of a reaction stack and the flow of catalyst, reactants, and heat exchange medium therethrough.

FIG. 4 is cross-section of the reaction stack taken along line 4—4 of FIG. 3.

DETAILED DESCRIPTION OF THE INVENTION

Figure 1:
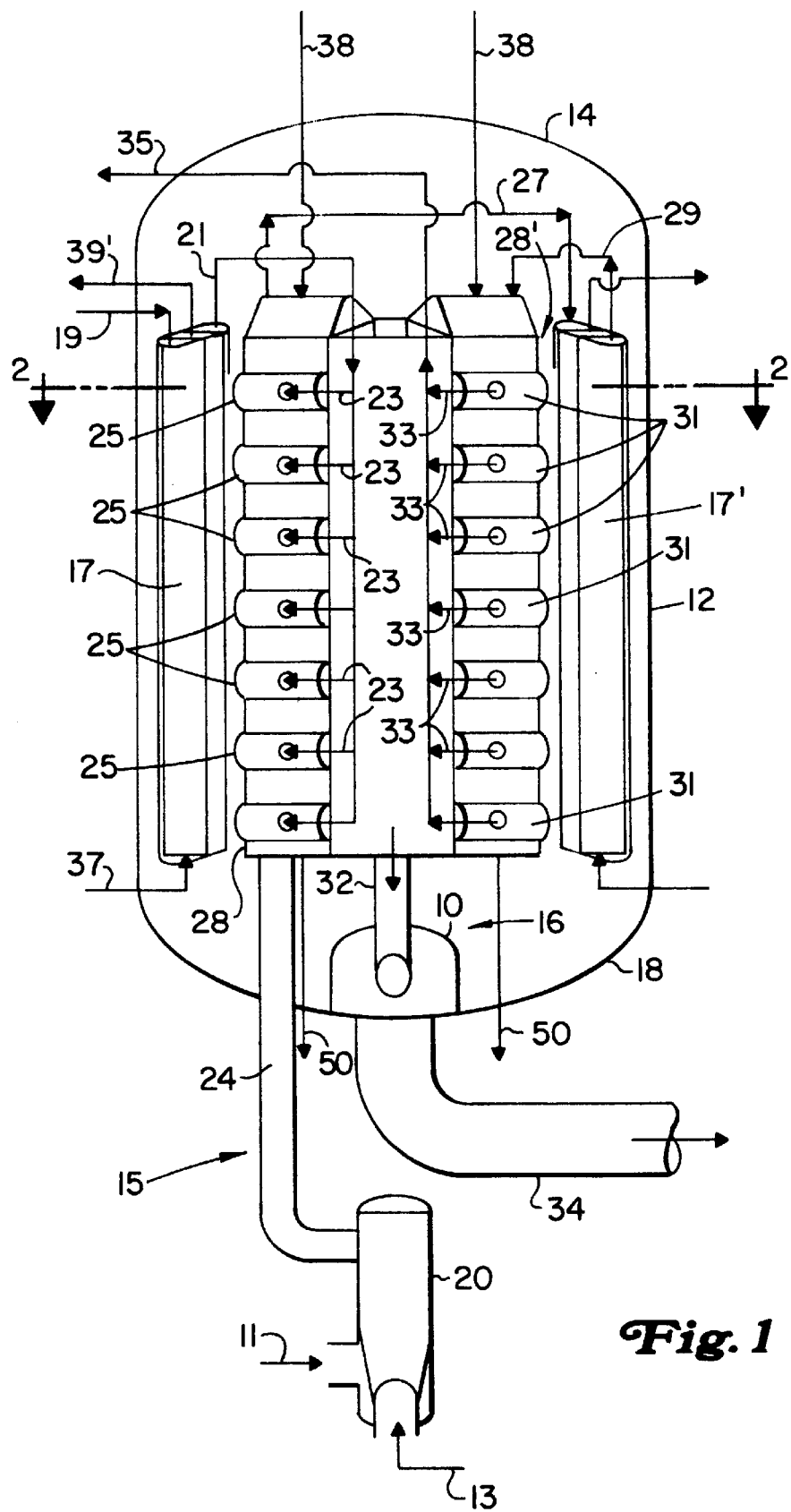
FIG. 1 is a sectional elevation of a reactor arranged in accordance with this invention.

The process may be useful in a wide variety of catalytic reactions. Suitable processes may use heterogeneous or homogeneous catalysts. Suitable reaction zone arrangements may also employ catalyst beds that are fixed, moving, or fluidized beds. This invention is most beneficially applied to catalytic conversion processes having high endothermic heats of reaction. Reactions of this type include the reforming of hydrocarbons and the dehydrogenation of hydrocarbons. This invention may be applied to processes having high exothermic heats of reaction such as hydrocarbon oxidation, ammonia synthesis, phthalic anhydride production, and ethylene oxide formation.

Most catalysts for the reaction of hydrocarbons are susceptible to deactivation over time. Deactivation will typically occur because of an accumulation of deposits that cause deactivation by blocking active pore sites or catalytic sites on the catalyst surface. Where the accumulation of coke deposits causes the deactivation, reconditioning the catalyst to remove coke deposits restores the activity of the catalyst. Coke is normally removed from the catalyst by contact of the coke-containing catalyst at high temperature with an oxygen-containing gas to combust or remove the coke in a regeneration process. The regeneration process can be carried out in situ or the catalyst may be removed from a vessel in which the hydrocarbon conversion takes place and transported to a separate regeneration zone for coke removal. Arrangements for continuously or semi-continuously removing catalyst particles from a bed in a reaction zone for coke removal in a regeneration zone are well known. U.S. Pat. No. 3,652,231 describes a continuous catalyst regeneration process which is used in conjunction with catalytic reforming of hydrocarbons, the teachings of which are hereby incorporated by reference. In the case of the reaction zone, the catalyst is transferred under gravity flow by removing catalyst from the bottom of the reaction zone and adding catalyst to the top. U.S. Pat. No. 5,073,352 and U.S. application Ser. No. 09/058,606 filed Apr. 10, 1998, now abandoned, describes a method and apparatus for moving catalyst through channel reactors.

The reaction zones for the process of this invention may indirectly contact the reactants with the heat exchange fluid in any relative direction. Thus, the flow channels, inlets, and outlets of the reaction zones may be designed for co-current, counter-current, or cross-flow of reactant relative to the heat exchange fluid. Cross-flow of reactants is used reduce the flow path length through the reactor thereby minimizing the pressure drop associated with the flow of reactants through the reactor and simplifying mechanical design. For this reason, a cross-flow arrangement can be used to provide the reactants with a shorter flow path across the reaction zone.

Preferred process arrangements for practicing this invention will pass reactants in co-current-flow with respect to the heat exchange fluid. Co-current flow offers the best compatibility with most process kinetics. More heat is usually released or absorbed by the process reaction near the inlet of the reaction zone. Co-current flow favors high heat transfer near the inlet of the reaction of the reaction zone.

The shorter flow path reduces overall pressure drop of the reactants as they pass through catalyst particles retained in the reactor. Lower pressure drops can have a two-fold advantage in the processing of many reactant streams. Increased flow resistance i.e., pressure drop, can raise the overall operating pressure of a process. In many cases, product yield or selectivity is favored by lower operating pressure so that minimizing pressure drop will also provide a greater yield of desired products. In addition, higher pressure drop raises the overall utility and cost of operating a process.

It is also not necessary to the practice of this invention that each reactant channel be alternated with a heat exchange channel. Possible configurations of the reaction section may place two or more heat exchange channels between each reactant channel to reduce the pressure drop associated with the circulation of the heating medium. When used for this purpose, a plate separating adjacent heat exchange channels may contain perforations.

The type and details of the reactor arrangement contemplated in the practice of this invention are best appreciated by reference to the drawings. FIG. 1 is a schematic representation of a catalytic reactor section designed to effect a catalytic reaction on a reactant fluid while using indirect heat exchange with a heat transfer fluid to maintain favorable reaction temperatures as the reactant fluid flows through the reaction section. The reactor contains multiple reaction stacks. The reactor section contains means for sequentially reheating the heating fluids as it flows out of the reactor sections of each reaction stack. The reactor effects catalytic reaction of a flowing reactant fluid under controlled temperature conditions by indirect contact with a flowing heat transfer fluid. Movement of catalyst through the reaction stacks is possible, but usually requires the reduction or stoppage of the reactant flow before the particulate catalyst can move.

Figure 2:
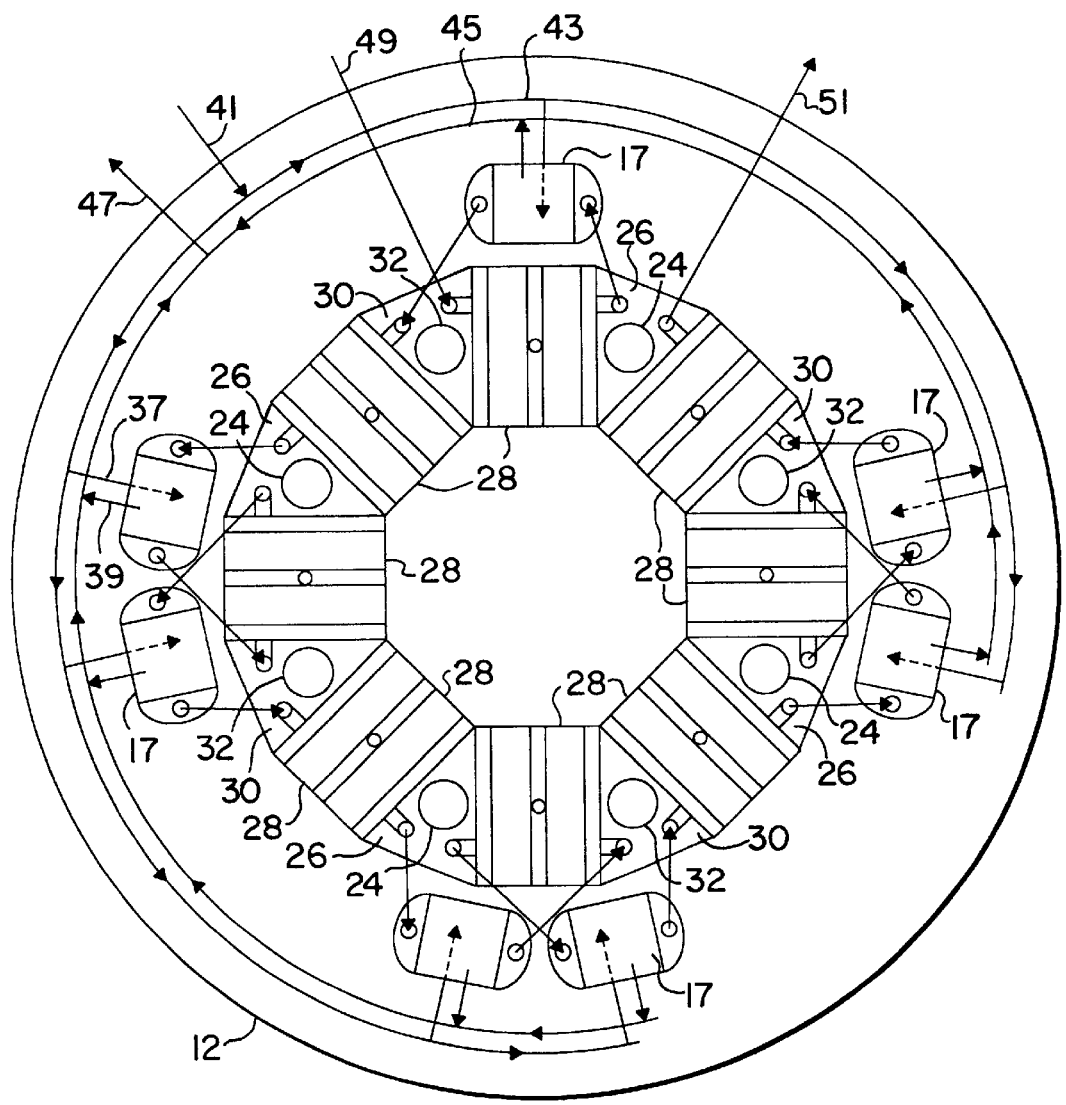
FIG. 2 is a section taken along line 2—2 of FIG. 1

The reactor section comprises a reactor vessel 12 having a circular cross-section. The reactor vessel 12 has an elliptical head 14. Another elliptical head 18 closes the bottom of reactor vessel 12 and supports a plenum 10 of a withdrawal system. Reactants and steam flow through inlets 11 and 13 into a manifold 20 that provides part of a distribution system 15 for disiributing the reactants into reactant inlet pipes 24. As shown in FIG. 2, reactant inlet pipes 24 feed the reactant stream into a distribution space 26. Reactants flow horizontally across reaction stacks 28 through vertically extended reactant flow channels defined therein. A collection space 30 collects reaction products from the reactant channels. Collector pipes 32 withdraws the reaction products from each collection space 30 into a withdrawal system 16 (see FIG. 1) that transports the reaction products out of the reactor vessel via a line 34. In the arrangement of FIGS. 1 and 2, each reactant inlet pipe 24 supplies reactants to two reactant stacks 28 while each outlet pipe 32 withdraws reactant products from two reaction stacks 28. The offsetting of the reactant inlet pipes 24 to the outlet pipes 32 results in each outlet pipe 32 withdrawing reactants supplied by two different reactant inlet pipes 24.

Looking again at FIG. 1, the reactor 12 also contains heaters 17 and 17' for reheating the heating fluid as it passes from one reaction stack (28 or 28') to the next. Looking again at FIG. 1, cold heating fluid enters reactor 12 through a line 19 and passes through a first heater 17. A line 21 passes the heated fluid to a series of delivery conduits 23 that deliver the heating fluid to the reaction stacks 28 via heat transfer manifolds 25. Heat transfer manifolds deliver the heating fluid to the heating channels in reaction stacks 28. Another series of collection manifolds (not shown) withdraw the cooled heating fluid from the reaction stack 28 and deliver it to an intermediate conduit system comprising an inlet conduit 27 and an outlet conduit 29. Intermediate conduits 27 and 29 reheat the heating fluid in another heater 17'. Heated fluid from heater 17' passes into reaction stack 28' via another series of delivery conduits and distribution manifolds (not shown). A plurality of collection manifolds 31 spaced down reaction stack 28' recover the heating fluid through a plurality of recovery conduits 33 that deliver the heating fluid to a central recovery conduit 35. Recovery conduit 35 will typically return at least a portion of the heating fluid back to inlet conduit 19. Recovery conduit 35 recovers the heating fluid from the reaction stack 28' that is in an end position. Inlet conduit 21 delivers the heat exchange fluid to a reaction stack that is in a lead position. If any intermediate reaction stacks are provided, similar piping would move the heating fluid out of one reaction stack to an intermediate feeder and into another reaction stack.

FIG. 2 shows that an additional layout arrangement for supplying a super heating fluid to the different heaters 17 and the interconnecting piping between the reaction stacks 28. The external heating fluid may be supplied to the heaters 17 via a line 41.

The intermediate heating provided between the reaction stacks may be provided externally to the reaction zone, but is preferably provided as shown in FIGS. 1 and 2 by internal heaters. The internal heaters may be in the form of indirect heat exchangers, fired heaters or simply a system for introducing fuel into the heat exchange media for in-situ combustion which again reheats the heat exchange fluid. For example, the heater may comprise an injector that injects a combustion reactant into the intermediate conduit. Containing the heaters within the reactor provides an overall benefit of maintaining heating efficiency by performing the heat exchange within the reaction vessel to minimize or eliminate heat loss to the atmosphere associated with the reheating of the fluid passing through reaction stacks.

Where heaters 17 provide indirect heat exchange, a heating fluid 37 enters the heater 17 and exits after indirect heat exchange via a conduit 39'. The heater 17 may be any form of indirect heat exchange or that will provide an efficient heat exchange between the external heat exchange fluid and the internal heating fluid that passes through the reaction stacks. A distribution header 43 delivers the fluid for reheating the heating fluid to the individual heaters 17. Another collection header 45 recovers the cooled reheating fluid from the heater 17 and withdraws it from the reaction vessel 12 through a line 47. FIG. 2 also shows the heating fluid entering the reaction vessel 12 through a line 49 into the reaction stack 28 in the lead position and the withdrawal of heating fluid via a line 51 from the reaction stack in the end position.

The reactant stream typically contacts a particulate catalyst in each of the reaction stacks. The catalyst will usually be present as discrete particles usually in a size range of from 1 to 15 mm in diameter. The particles may have any shape, but they will typically comprise spheres or cylinders. Catalyst for passage into the reactant channels enters the reaction stacks 28. Catalyst enters the top of the reactor vessel 12 through catalyst loading conduits 38 after passage through the reaction channels in reaction stacks 28, catalyst flows out of the reaction stacks 28 and reaction vessel 12 through catalyst transfer pipes 50.

The arrangement and operation of the reaction stacks is shown more clearly by a schematic representation in FIGS. 3 and 4. Each reaction stack 28 comprises a plurality of parallel plates 72 as shown in FIG. 4. Suitable plates for this invention will comprise any plates that allow a high heat transfer rate. Thin plates are preferred and usually have a thickness of from 1 to 2 mm. The plates are typically composed of ferrous or non-ferrous alloys such as stainless steel. Each plate 72 may be smooth, but preferably has corrugations that are straight or inclined to the flow of reactants and heat exchange fluid. The plates may be formed into curves or other configurations, but flat plates are generally preferred for stacking purposes. The corrugated plates may be stacked directly next to each other with the space between corrugations defining alternate reactant channels 73 and heat exchange channels 74. Where plates 72 contain inclined corrugations, the plates may be stacked next to each other to define the heat exchange and reactant flow channels as the area between corrugations. Preferably the corrugation pattern will be reversed between adjacent plates so that a herring bone pattern on the faces of opposing corrugated plates will extend in opposite directions and the opposing plates faces may be placed in contact with each other to form the flow channels and provide structural support to the plate sections.

FIG. 3 shows a modified arrangement of delivery and collection manifolds for the reaction stacks 28. This modified arrangement moves the heating fluid in a vertical down flow direction as opposed to the horizontal flow shown in FIGS. 1 and 2.

The heating fluid enters the process through an inlet header (not shown) that distributes the heating fluid to distribution pipes 66. Distribution pipes 66 supply heat exchange fluid to a heat exchange manifold 64 at the bottom of each reaction stack 28 The heat exchange fluid flows vertically down the heat exchange channels in each reaction stack into a collector manifold 62 at the bottom of each heat exchange stack 28. Collection pipes 60 feed the heat exchange fluid into a collection manifold (not shown) which withdraws heat exchange fluid.

Each reaction stack includes in its upper part an inlet for receiving the heat exchange fluid into circulation system "B". The inlet may be a single opening. FIGS. 3 and 4 show the manifolds 64 and 62 for distributing and collecting heat exchange fluid from the top and the bottom, respectively of reaction stack 28. Manifolds 64 and 62 communicate with the heat exchange channels 74 through openings in the sides 77 that are located at the top and bottom on opposite sides of the reaction stack. The manifolds provide a distribution area on the sides of the reaction stack. In the distribution area covered by manifolds 64 and 62, the sides 76 of the reactant channels are closed to prevent the entry of the heat exchange fluid into the reactant channels.

Catalyst particles 75 normally fill the reactant flow channels 73. The sides 76 of reactant flow channel 73 are closed to catalyst flow by a permeable closure 76 that still permits the flow of reactants in the direction indicated by arrows "A". The sides 77 of heat exchange channels 74 have a fluid impermeable closure that holds the heat exchange fluid over the length of channel 74. The tops of the heat exchange channels are closed to prevent catalyst entry therein. As shown in the reaction stack of FIG. 3, the heat exchange fluid flows downwardly as indicated by arrows "B" such that the reaction stack defines a specific circulation system for flows "A" and "B" wherein the reactant stream "A" and the heat exchange fluid "B" flow in crosswise directions and through alternate channels formed by adjacent plates 72.

Catalyst particles 75 flow into the top of reactant channel 73 through diffuser 52. Diffuser 52 may contain internal baffles or corrugations 78 for distributing catalyst evenly across the top of the reactant channels. Similarly, collector 54 at the bottom of reactant channel 73 collects the catalyst particle 75 and may contain baffles or corrugations 80. The baffles or corrugations in the diffuser and collector promote a uniform replacement of catalyst across the entire horizontal length of each reactant channel 73.

Figure 5:
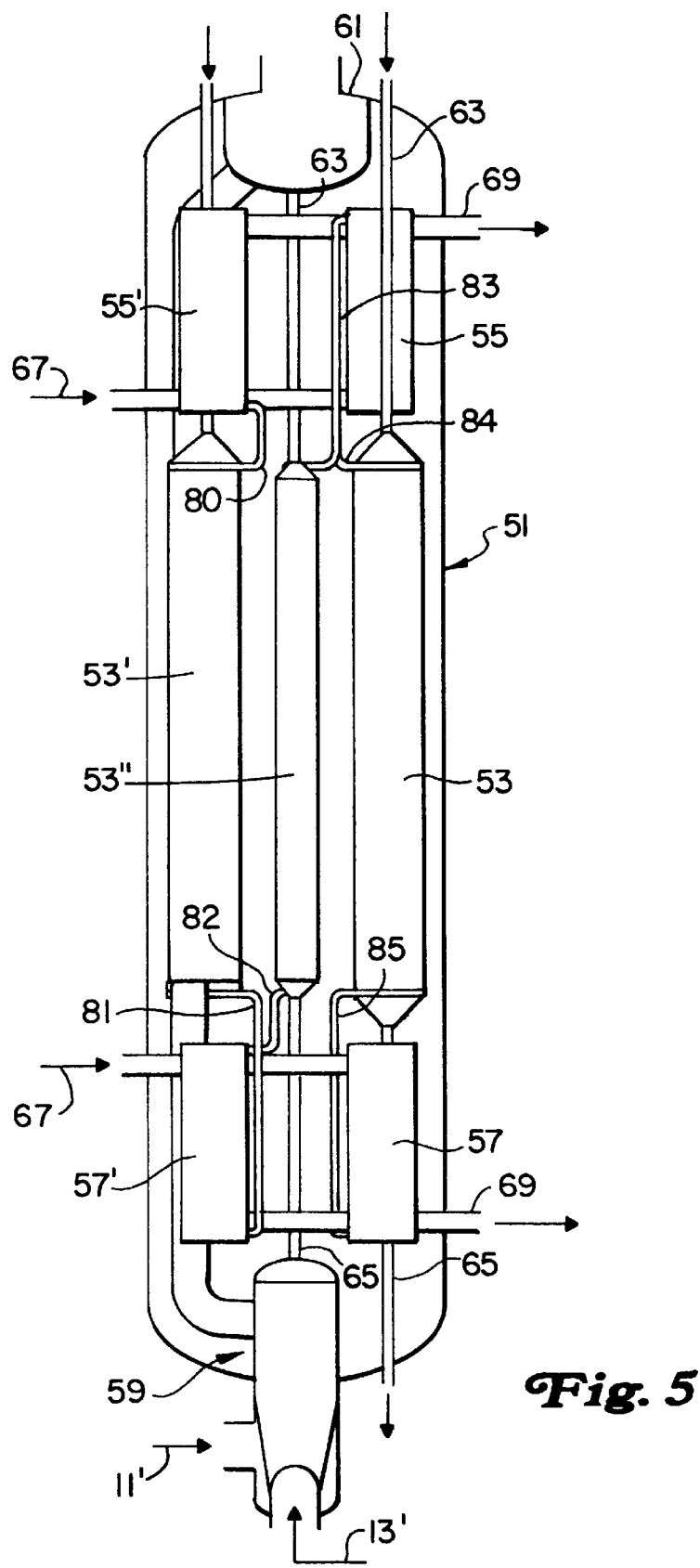
FIG. 5 is sectional elevation of a reactor arranged in accordance with this invention and modified from FIG. 1.

The reactor arrangement may be modified to place the heaters in different locations. FIG. 5 shows an arrangement of a reaction vessel 51 having a plurality of reaction stacks 53. The arrangement locates heaters 55 above the reaction stacks and heaters 57 below the reaction stacks. In a manner similar to that previously described in conjunction with FIGS. 1 and 2, mixed feed enters the bottom of the reactor system through a distribution system 59 that receives reactant and steam from lines 11' and 13' respectively. A withdrawal system 61 collects reacted reactants from the top of the reaction stack for withdrawal from the reactor 51. Catalyst may again be added and withdrawn from the reactor vessel 51 through upper conduit 63 and lower conduit 65. Heaters 55 and 57 receive a super heating stream from line 67 that is distributed to the heaters. A conduit 69 collects the cooled stream of heat exchange fluid after it passes through heaters 55 and 57. Heaters 57 provide indirect heat exchange with the reheating fluid supplied by conduits 67.

The heating fluid may be circulated between heaters 55 and 57 and reaction stacks 53 in any desired manner. In the arrangement of FIG. 5 heated heating fluid flows out of heater 55' through a conduit 80 and downwardly through reaction stack 53'. A lower conduit 81 recovers the cooled heating fluid and passes it to the bottom of heater 57'. Heater 57' reheats the heating fluid by heat exchange with the reheat fluid from line 67. The hot heating fluid flows into the bottom of reaction stack 53" via a line 82. The heating fluid flows upwardly through channels in reaction stack 53". An intermediate conduit 83 transfers cooled heating fluid from the top of reaction stack 53" to the top of heater 55. Reheat fluid 67 again heats the heating fluid as it passes downwardly through heater 55. Reheat fluid passes from heater 55 to reaction stack 53 through a conduit 84. The circulation of heating fluid continues in a similar manner as it leaves the bottom of reaction stack 53 through a conduit 85 and passes into the bottom of heater 57. In this manner, the circulation of the heating fluid changes direction through each reaction stack 53 while passing downwardly through each heater 55 and 57.

Figure 6:
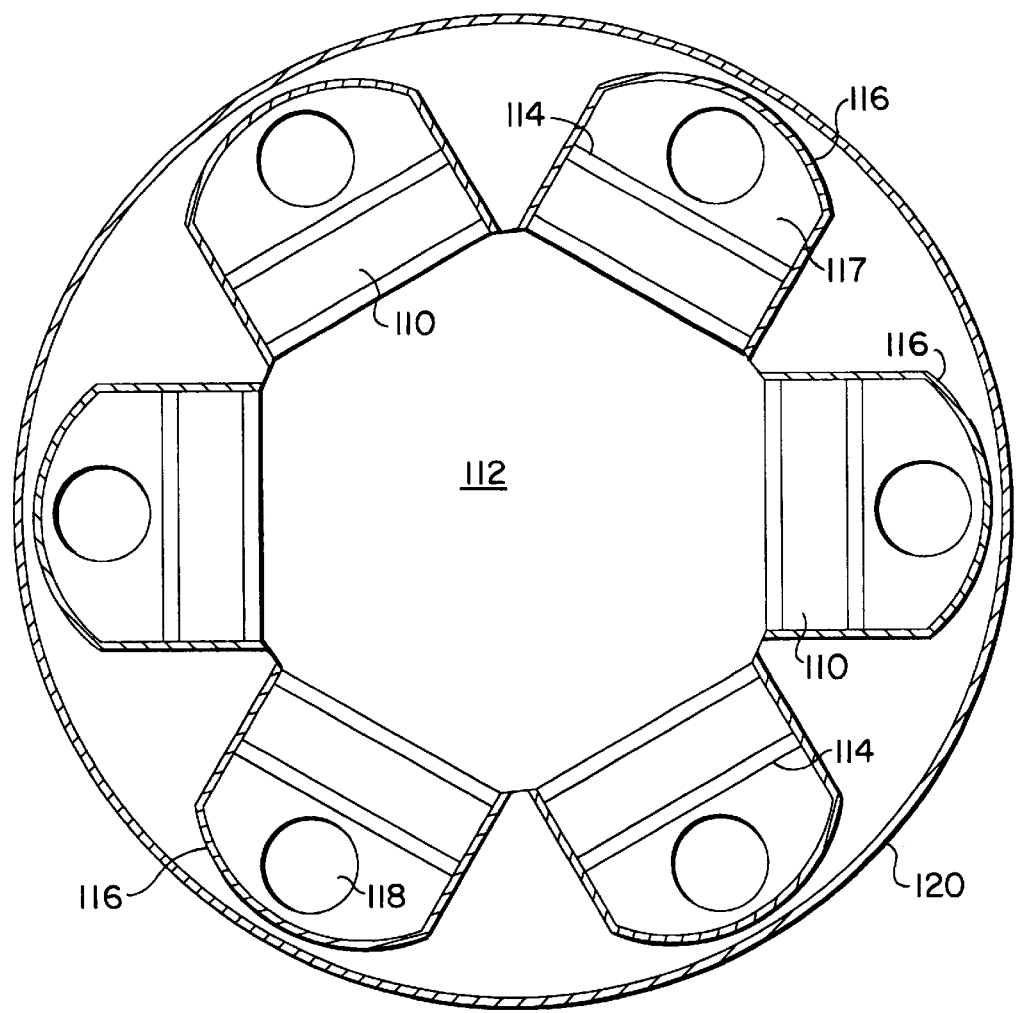
FIG. 6 shows a horizontal cross-section of a reactor containing reaction stacks similar to those shown in FIGS. 1–4, in an alternate arrangement.

In addition to the heat exchange circulation, the process may be operated in a variety of other ways. Flow into the reaction stacks or out of the reaction stacks may be arranged to control multiple reaction stacks at one time as shown by the embodiment of the invention in FIGS. 1–5. The arrangement of the reaction stacks may also be modified to have central collection or distribution of reactants with withdrawal from the periphery. Alternately, the flow of reactants into or products out of each reaction stack may be individually controlled. An arrangement for the radial flow of reactants into or out of each reaction stack is shown in FIG. 6. FIG. 6 shows a horizontal cross-section of a reactor containing reaction stacks similar to those shown in FIGS. 1–5. FIG. 6 differs from FIGS. 1–5 in that the reaction stacks 110 are arranged circumferentially in a polygonal arrangement around a central space 112 that can serve as a distributor or as a collector. A baffle 116 surrounds the outside 114 of each reaction stack 110. Baffle 116 again defines a space at the outside of each reaction stack 110 that can serve as a collector or distributor. Individual pipe openings 118 communicate with the outer space 117 enclosed by each baffle 116. Appropriate valving on the piping to outlet 118 can selectively restrict or stop flow through each individual reaction stack. All of the reaction stacks may again be surrounded by a reaction vessel 120 to provide pressure containment for the reaction.

The arrangement of this invention can be particularly suited for the dehydrogenation of paraffinic feedstocks. The dehydrogenation of ethylbenzene to produce styrene is well known. Paraffinic feedstocks ordinarily have from about 3 to about 18 carbon atoms. Particular feedstocks will usually contain light or heavy paraffins. A catalytic dehydrogenation reaction is normally effected in the presence of catalyst particles comprised of one or more Group VII noble metals (e.g., platinum, iridium, rhodium, and palladium) combined with a porous carrier such as a refractory inorganic oxide. Alumina is a commonly used carrier. Dehydrogenation conditions include a temperature of from about 400° to about 900° C., a pressure of from about 0.01 to 10 atmospheres, and a liquid hourly space velocity (LHSV) of from about 0.1 to 100 hr$^{-1}$. Generally, the lower the molecular weight of the feed the higher the temperature required for comparable conversions. The pressure in the dehydrogenation zone is maintained as low as practicable, consistent with equipment limitations, to maximize the chemical equilibrium advantages. The preferred dehydrogenation conditions of the process of this invention include a temperature of from about 400° to 700° C. and a pressure from about 0.1 to 5 atmospheres. Additional information on the dehydrogenation of paraffins can be found in U.S. Pat. Nos. 4,677,237, 4,880,764, and 5,087,792.

This invention is particularly adapted for the production of styrene by the dehydrogenation of ethylbenzene using a heating fluid to maintain the temperature of the reaction zone at favorable condition for selectivity and conversion. In a typical arrangement such as that shown in FIGS. 1–5, the total ethylbenzene feed enters in parallel to each of each reaction stacks containing catalyst. The feed has a fixed steam-to-ethylbenzene ratio. The heating fluid enters in co-current flow with respect to the feed throughout the reactor length and passes along the surface of each bundle in series inside the reaction stacks. The heat transfer fluid upon leaving a single reaction stack is reheated to the appropriate temperature before entering the next reaction stack. The reaction stacks can use a variety of different heat transfer fluids such as liquid sodium, flue gas, steam, or even selective oxidation of the hydrogen that is produced through the dehydrogenation process. The combustion of the hydrogen from the dehydrogenation may take place in the heaters and provide the heating fluid for indirectly reheating the heating fluid that circulates through the reaction stacks and the heaters.

More specifically, in such an arrangement, an ethylbenzene feed would enter parallel channel paths of the reaction stacks. As feed passed along the reaction stack, flow paths would contact the dehydrogenation catalyst. Heat from the heating fluid would pass across the heat transfer plates from the heating channel to the reaction channel. A mixture of ethylbenzene, styrene, and hydrogen generated from the dehydrogenation reaction would exit the reactor.

Conditions for the dehydrogenation of ethylbenzene to produce styrene is well known. A catalytic dehydrogenation reaction is normally effected in the presence of an iron oxide catalyst. Suitable catalysts comprising at least 35 wt-% iron oxide are described in U.S. Pat. Nos. 3,387,053. 4,467,046 describes a benzene dehydrogenation catalyst that contains 15 to 30 wt-% potassium oxide, 2 to 8 wt-% cerium oxide, 1.5 to 6 wt-% molybdenum oxide, 1 to 4 wt-% calcium carbonate, with the balance comprising iron oxide. Ethylbenzene dehydrogenation conditions include a temperature of from about 400° to about 900° C., a pressure of from about 0.01 to 10 atmospheres, and an LHSV of from about 0.1 to 2 hr$^{-1}$. The pressure in the dehydrogenation zone is maintained as low as practicable, sometimes under vacuum, consistent with equipment limitations, to maximize the chemical equilibrium advantages. The preferred dehydrogenation conditions of the process of this invention include a temperature of from about 400° to 700° C. and a pressure from about 0.1 to 5 atmospheres.

In a preferred form of a styrene production process, a super-heated steam stream would enter the heaters via a distribution header and the super-heated steam will usually be added in a quantity that will produce a steam-to-ethylbenzene ratio of approximately 0.5 to 2, and more preferably 0.7 to 1.5 at the inlets to reaction channels. Passage of the stream through the channels of the heater efficiently heats the heating fluid by virtue of the large surface area provided by heat transfer plates. Manifold space redistributes the stream after it passes through the heaters and mixes it with the entering ethylbenzene feed to promote the dehydrogenation reaction of the steam and ethylbenzene mixture as it passes into the reaction channels. Some form of pipe distributor may be useful to distribute the ethylbenzene feed. The reaction channels contain an ethylbenzene dehydrogenation catalyst. Catalyst material may reside in the channels as a coating applied to the plates or as discrete particles retained in the channels by an appropriate. screen material across inlets. Indirect heating across plates by the heating fluid compensates for the cooling effect of the endothermic dehydrogenation reaction as the ethylbenzene and steam mixture passes up reaction channels.

A collection space collects the dehydrogenation zone product stream from the reaction channels. The collected reactor effluent mixture of styrene, ethylbenzene, and steam is transferred into a product line for recovery of product components and recycle of reactants and steam. The effluent stream from the dehydrogenation zone generally will contain unconverted hydrocarbons, hydrogen, and the products of dehydrogenation reactions. This effluent stream is typically cooled and passed to a hydrogen separation zone that separates a hydrogen-rich vapor phase from a hydrocarbon-rich liquid phase. Generally, the hydrocarbon-rich liquid phase is further separated by means of a suitable selective solvent, a selective reaction or reactions, or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds. Additional information related to the operation of dehydrogenation catalysts, operating conditions, and process arrangements can be found U.S. Pat. No. 5,043,500, the contents of which are hereby incorporated by reference.

Passing the super-heated stream through the heaters raises the temperature of the circulating heating fluid between each reaction stack. In this manner, the super-heated steam may have temperatures higher than the sensitivity temperature that would cause decomposition of the styrene products and may also require special metallurgy that will allow higher operating temperature, but the need for expensive metallurgy is limited to only the heaters for reheating, which greatly reduces the overall cost of providing the reaction stacks for the heat exchange type reaction arrangement. Preferably, the heating fluid is a high capacity heat transfer fluid that moderates the temperature of the steam as it cools in the heaters so that the dehydrogenation reaction occurs at an essentially uniform temperature in the reaction stacks.

EXAMPLES

These examples compare the overall start of run yield estimates between a traditional two-reactor styrene process and a styrene process in accordance with this invention that uses eight parallel pass reaction stacks. These examples are generated from computer simulations of models for the specific operation of a styrene process using known kinetic parameters of the dehydrogenation reactions along with experimentally verified heat transfer coefficients across the common boundary of the reaction in heating channels to provide the results. The kinetic information is based on activities for that of a commercial iron oxide type dehydrogenation catalyst.

Example I

Figure 7:
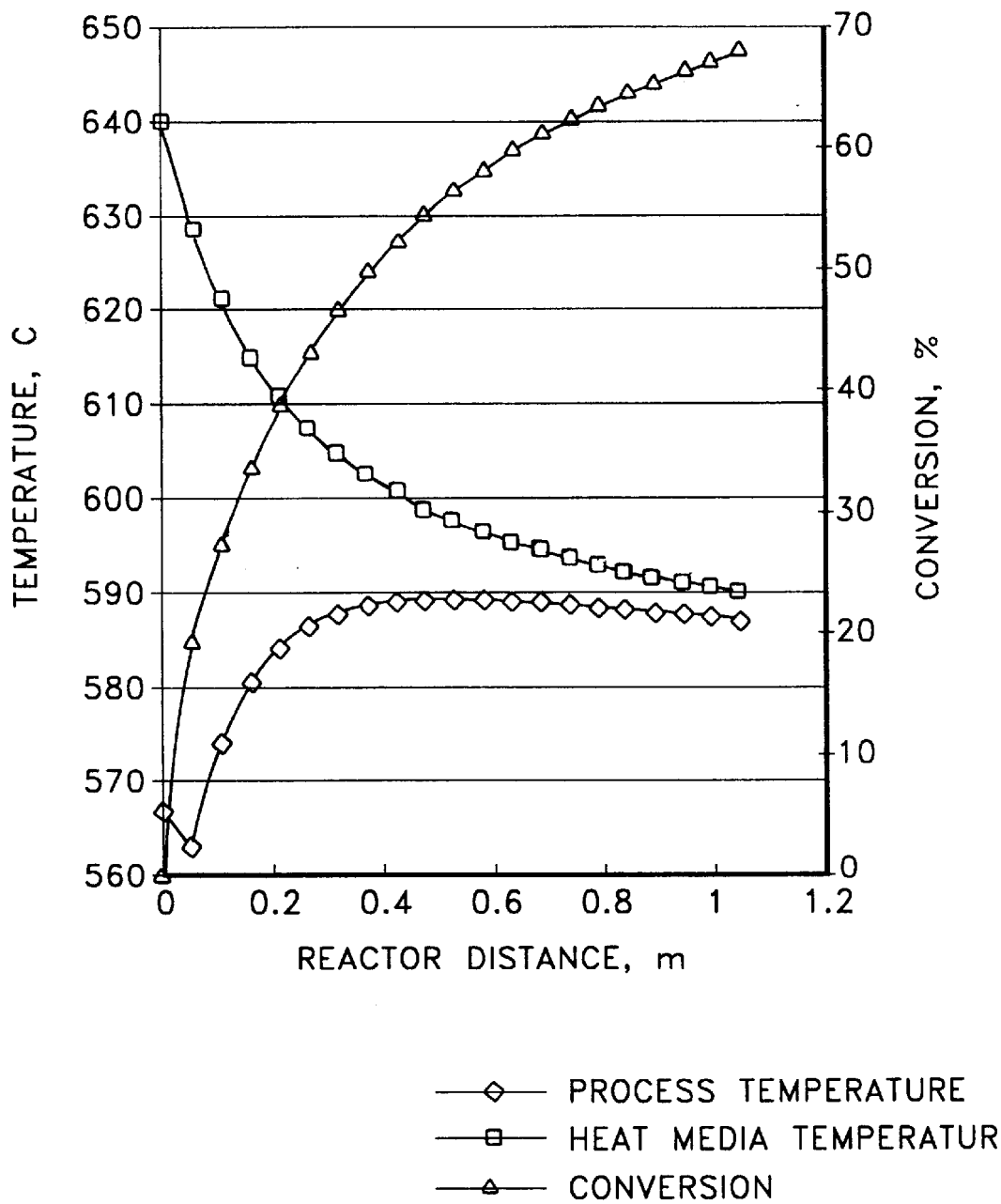
FIGS. 7 and 8 are graphs showing the performance of a traditional styrene production system.
Figure 8:
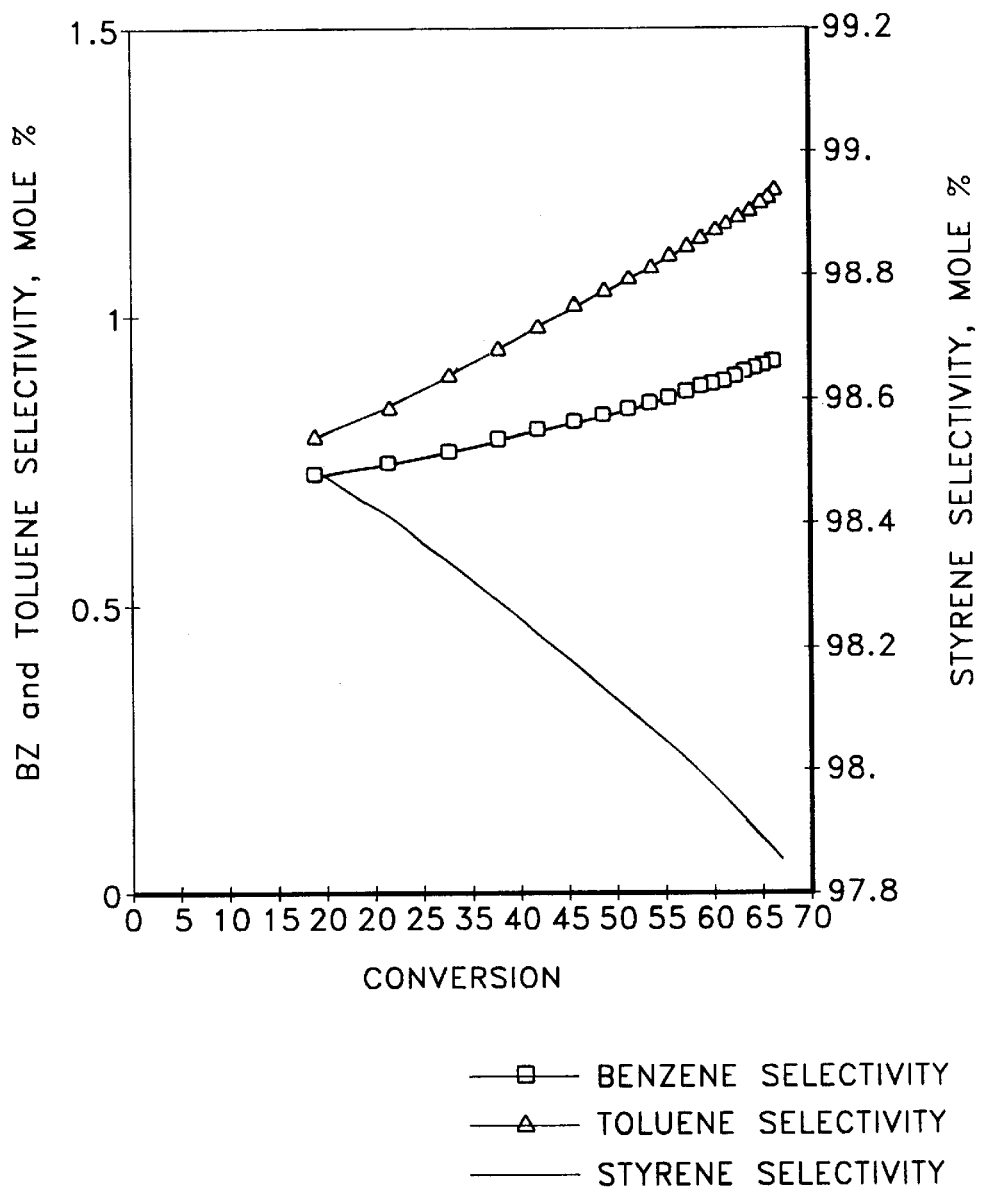

This example operates two reactors in series in an adiabatic manner. The process temperature and pressure at the inlet and outlet of each reactor, as well as the composition of the feed stream entering and exiting the two reactors is shown in Table 1. The process passes each reactant stream through the reactors at an LHSV of 1 and a catalyst volume in each reactor of about 92 cubic meters. The catalyst was ⅛-inch size extrudite that was loaded to avoid fraction of about 0.45. The particles had a Reynolds Number of 48. The feed entered at a steam-to-oil ratio of 1.35. Ethylbenzene conversion in the first reactor was 40.4%, and in the second reactor 68%. The styrene selectivity from the second reactor was 97.84 mol-%. FIGS. 7 and 8 show the conversion and selectivity performance for the overall process.

Example II

Figure 9:
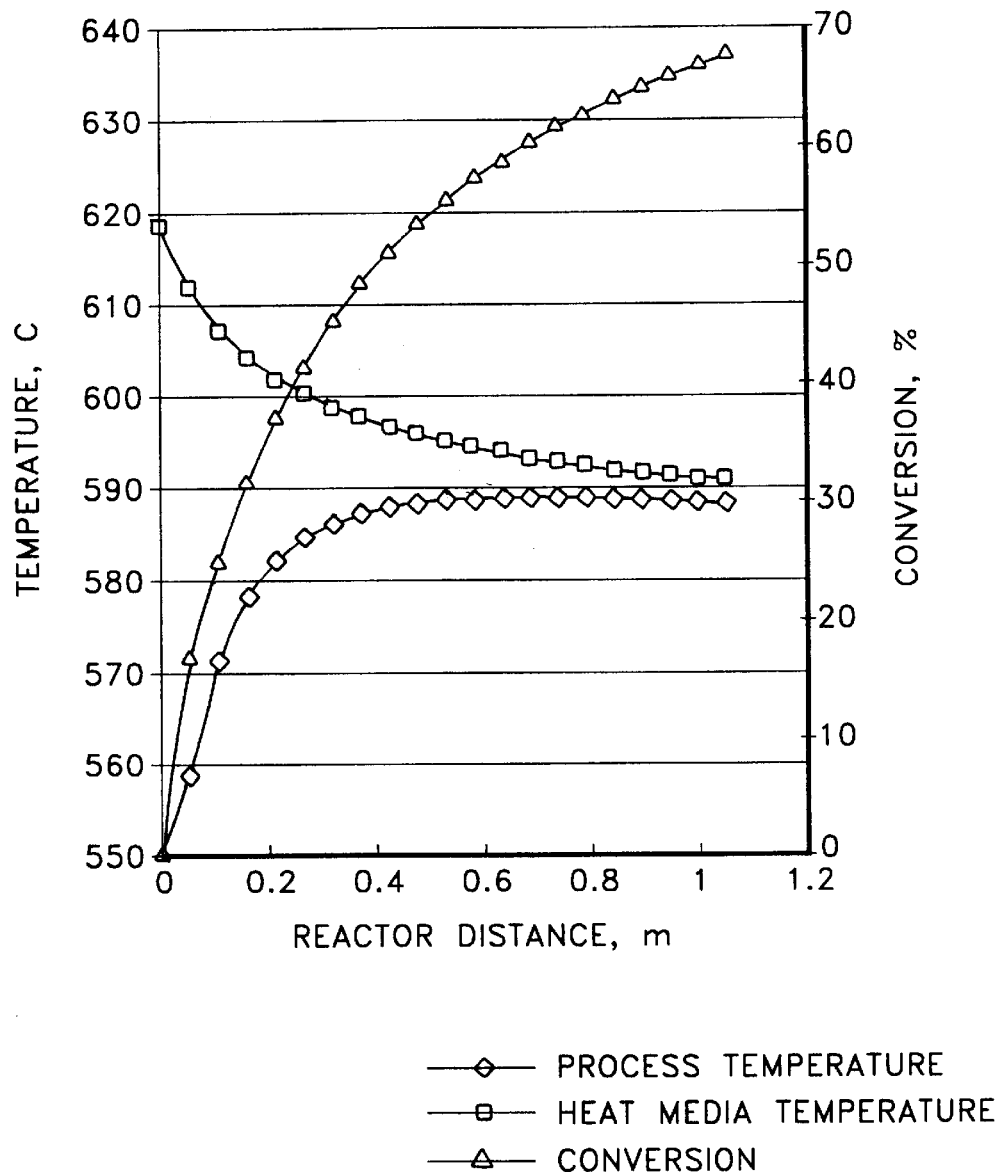
FIGS. 9 and 10 are graphs showing the performance of the reactor arrangement of this invention for the production of styrene.
Figure 10:
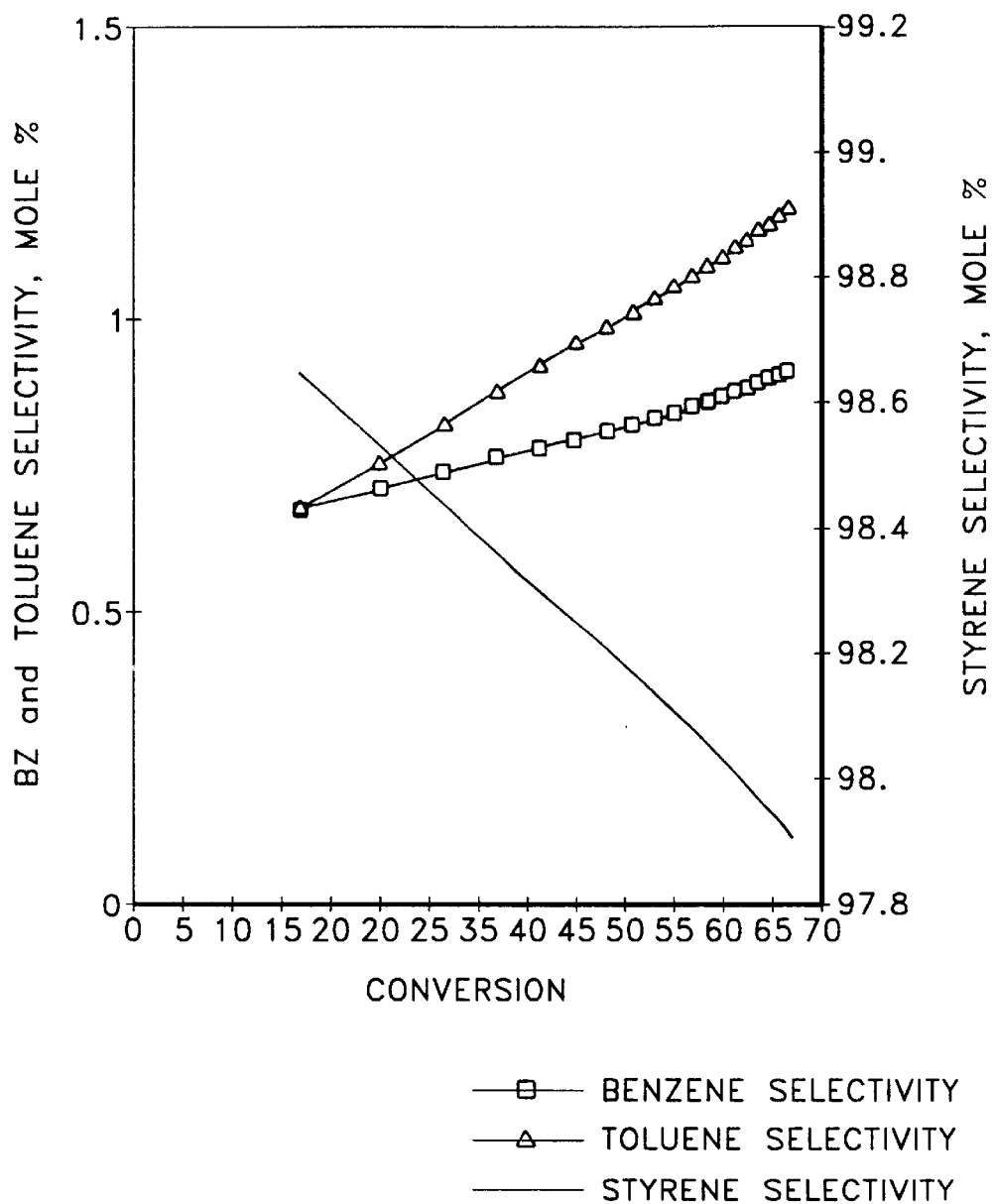

This example passes the feed stream having the composition given in Table 2 as eight separate streams to eight parallel reaction stacks. The reaction stacks provide a reactant path length 1.05 meters and a heating fluid path length of the 13 meters. The arrangement uses a total of 672 process channels and 680 heating channels. The catalyst has essentially the same properties as those used in Example I. The steam-to-oil ratio for the feed is 1. Table 2 also shows the inlet and outlet temperatures for each of the reaction stack which operated at essentially the same conditions. The process circulated the heat transfer fluid through each of the reaction stacks that entered at a temperature of 640° C. and left each reaction stack at a temperature of 590° C. Intermediate heating of the heating fluid as it passed in series flow through the reaction stacks provided recovery of the inlet temperature to 640° C. The heat transfer media had a total flow rate of 79,400 kg/hr. Results for selectivity and conversion using the intermediate reheat arrangement of Example 3 is shown in FIGS. 9 and 10.

Example II was simulated for both a steam heating fluid and a liquid sodium heating fluid. When using the steam heating fluid, a selectivity increase of 0.8 mol-% was observed. When using the liquid sodium as the heat transfer fluid, a maximum 1.2 mol-% increase in the selectivity was observed. The catalyst bed size could also be reduced by 50% when compared to a traditional styrene process.

TABLE 1

|  | Reactor No. 1 Inlet | Reactor No. 1 Outlet | Reactor No. 2 Inlet | Reactor No. 2 Outlet |
|---|---|---|---|---|
| Process Temperature, °C. | 610 | 529 | 619.3 | 564 |
| Process Pressure, psig | −5.9 | −7.03 | −7.497 | −8.6 |
| Components, kg/hr |  |  |  |  |
| Ethylbenzene | 78130 | 46555 | 46555 | 24994 |
| Styrene | 635 | 30857 | 30857 | 51227 |
| Benzene | 64 | 269 | 269 | 461 |
| Toluene | 564 | 983 | 982 | 1443 |
| Hydrogen | 0 | 608 | 608 | 1036 |
| Methane | 0 | 50 | 50 | 91 |
| Ethylene | 0 | 27 | 27 | 38 |
| Carbon Dioxide | 0 | 204 | 204 | 484 |
| Carbon Monoxide | 0 | 6 | 6 | 13 |
| Steam | 107619 | 107004 | 107004 | 106774 |
| Total | 186562 | 186562 | 186562 | 186562 |

TABLE 2

|  | Inlet | Outlet |
|---|---|---|
| Process Temperature, °C. | 567 | 587 |
| Process Pressure, psig | 7.3 | 8.7 |
| HTM Duty, MBU/hr | 66.86 |  |
| Components, kg/hr |  |  |
| Ethylbenzene | 78114 | 24980 |
| Styrene | 644 | 51645 |
| Benzene | 81 | 444 |
| Toluene | 564 | 1137 |
| Hydrogen | 0 | 1026 |
| Methane | 0 | 67 |
| Ethylene | 0 | 47 |
| Carbon Dioxide | 0 | 328 |
| Carbon Monoxide | 0 | 14 |
| Steam | 79397 | 79112 |
| Total | 158800 | 148800 |

What is claimed is:

1. A channel reactor apparatus for contacting reactants with a particulate catalyst, indirectly heating the reactants with a heating fluid and reheating the heating fluid with a reheating fluid, said apparatus comprising:

a plurality of reaction stacks with each reaction stack comprising a plurality of parallel plates extending vertically and horizontally and defining heating channels and reaction channels in each reaction stack;

a distribution system for passing a reactant stream to the reaction channels of each reaction stack in parallel flow;

a withdrawal system for collecting the parallel flow of reacted reactants from each reaction stack;

a heating fluid delivery conduit for delivering a heating fluid to the heating channels of one of the reaction stacks located in a lead position;

a plurality of intermediate conduits for passing the heating fluid in series flow from the reaction stack in the lead position, through the heating channels of reaction stacks located in an intermediate position, and to a reaction stack located in an end position;

a heating fluid recovery conduit for recovering the heating fluid from the reaction stack in the end position; and a heater for reheating the heating fluid as it passes through an intermediate conduit.

2. The apparatus of claim 1 wherein the apparatus includes means for adding catalyst particles to the top and withdrawing catalyst from the bottom of each reaction stack.

3. The apparatus of claim 1 wherein the heater comprises an exchanger for indirect heat exchange between the heating fluid and a superheating fluid.

4. The apparatus of claim 1 wherein the heater comprises an injector that injects a combustion reactant into the intermediate conduit.

5. The apparatus of claim 1 wherein a reaction vessel surrounds the reaction stacks and contains the heater.

6. The apparatus of claim 5 wherein at least a portion of the heaters is located above or below the reaction stacks.

7. The apparatus of claim 1 wherein the reaction stacks comprise a plurality of corrugated plates that define the heating channels and the reactant channels.

8. A channel reactor apparatus for contacting reactants with a particulate catalyst, indirectly heating the reactants with a heating fluid and reheating the heating fluid with a reheating fluid, said apparatus comprising:

a plurality of reaction stacks with each reaction stack comprising a plurality of parallel plates extending vertically and horizontally and defining heating channels and reaction channels in each reaction stack;

a distribution system for passing a reactant stream to the reaction channels of each reaction stack in parallel flow;

a withdrawal system for collecting the parallel flow of reacted reactants from each reaction stack;

a heating fluid delivery conduit for delivering a heating fluid to the heating channels of one of the reaction stacks;

a plurality of intermediate conduits for passing the heating fluid in series flow from the heating channels in one of the reaction stacks through the heating channels of another of the reaction stacks;

a heating fluid recovery conduit for recovering the heating fluid from one of the reaction stacks; and a heater for reheating the heating fluid as it passes through at least one of the intermediate conduits.

* * * * *